US012616755B1

(12) United States Patent
Wani et al.

(10) Patent No.: US 12,616,755 B1

(45) Date of Patent: May 5, 2026

(54) ANTIFUNGAL QUERCETIN CONJUGATES, METHODS OF PREPARATION AND USES THEREOF

(71) Applicant: Mohmmad Younus Wani, Jeddah (SA)

(72) Inventors: Mohmmad Younus Wani, Jeddah (SA); Waleed Ahmed El-Said, Jeddah (SA); Abdullah S. Al-Bogami, Jeddah (SA); Ziya Ahmad Khan, Jeddah (SA); Aijaz Ahmad, Johannesburg (ZA)

(73) Assignee: University of Jeddah, Jeddah (SA)

( * ) Notice: Subject to any disclaimer, the term of this patent is extended or adjusted under 35 U.S.C. 154(b) by 0 days.

(21) Appl. No.: 19/352,666

(22) Filed: Oct. 8, 2025

(51) Int. Cl.
*A61K 47/61* (2017.01)
*A61P 31/10* (2006.01)

(52) U.S. Cl.
CPC .............. *A61K 47/61* (2017.08); *A61P 31/10* (2018.01)

(58) Field of Classification Search
None
See application file for complete search history.

(56) References Cited

U.S. PATENT DOCUMENTS

2020/0069812 A1* 3/2020 Novak .................. A61K 47/64

OTHER PUBLICATIONS

Nguyen et al., Molecule 2497: 1-13 (Year: 2022).*
Shirani et al., International Journal of Biological Macromolecules 215: 234-345 (Year: 2022).*
Mukhopadhyay et al., Royal Society of Chemistry Advances 5: 97547-97562 (Year: 2015).*
Thombare et al., International Journal of Biological Macromolecules 88: 361-372 (Year: 2016).*
Ntow-Boahene., Frontiers in Bioengineering and Biotechnology 9: 1-14 (Year: 2021).*

* cited by examiner

*Primary Examiner* — Phuong Huynh
(74) *Attorney, Agent, or Firm* — WCF IP

(57) ABSTRACT

An antifungal compound/conjugate is derived from quercetin, a naturally occurring flavonoid, through a strategic conjugation approach. The resulting quercetin conjugate exhibits enhanced antifungal activity and improved pharmacological properties compared to its parent molecule. The conjugate demonstrates potent efficacy against a range of drug-resistant fungal pathogens, including *Candida auris*, a critical threat in clinical settings due to its multidrug resistance. The invention also encompasses methods for synthesizing the conjugate, formulating the conjugate in a pharmaceutical preparation, and methods of use for treatment and prevention of superficial and systemic fungal infections.

5 Claims, 13 Drawing Sheets
(5 of 13 Drawing Sheet(s) Filed in Color)
Specification includes a Sequence Listing.

SEQUENCE LISTING

```
Sequence total quantity: 24
SEQ ID NO: 1            moltype = DNA  length = 21
FEATURE                 Location/Qualifiers
source                  1..21
                        mol_type = other DNA
                        organism = synthetic construct
SEQUENCE: 1
gtcatcttgt tctccgaccg t                                                 21

SEQ ID NO: 2            moltype = DNA  length = 21
FEATURE                 Location/Qualifiers
source                  1..21
                        mol_type = other DNA
                        organism = synthetic construct
SEQUENCE: 2
ccagttgccg tcctttgtag a                                                 21

SEQ ID NO: 3            moltype = DNA  length = 21
FEATURE                 Location/Qualifiers
source                  1..21
                        mol_type = other DNA
                        organism = synthetic construct
SEQUENCE: 3
ttggcagatc tgtggttgtc c                                                 21

SEQ ID NO: 4            moltype = DNA  length = 21
FEATURE                 Location/Qualifiers
source                  1..21
                        mol_type = other DNA
                        organism = synthetic construct
SEQUENCE: 4
gacgccaata acaccacaag c                                                 21

SEQ ID NO: 5            moltype = DNA  length = 21
FEATURE                 Location/Qualifiers
source                  1..21
                        mol_type = other DNA
                        organism = synthetic construct
SEQUENCE: 5
ggtggtgctt tggatgttgt c                                                 21

SEQ ID NO: 6            moltype = DNA  length = 21
FEATURE                 Location/Qualifiers
source                  1..21
                        mol_type = other DNA
                        organism = synthetic construct
SEQUENCE: 6
caagtagtaa gcgtgctccc a                                                 21

SEQ ID NO: 7            moltype = DNA  length = 20
FEATURE                 Location/Qualifiers
source                  1..20
                        mol_type = other DNA
                        organism = synthetic construct
SEQUENCE: 7
tcaaccctta ccacggctac                                                   20

SEQ ID NO: 8            moltype = DNA  length = 20
FEATURE                 Location/Qualifiers
source                  1..20
                        mol_type = other DNA
                        organism = synthetic construct
SEQUENCE: 8
caccaccaca gacaagttgg                                                   20

SEQ ID NO: 9            moltype = DNA  length = 21
FEATURE                 Location/Qualifiers
source                  1..21
                        mol_type = other DNA
                        organism = synthetic construct
SEQUENCE: 9
```

-continued

```
atcttcaacc cttaccacgc c                                     21

SEQ ID NO: 10           moltype = DNA  length = 21
FEATURE                 Location/Qualifiers
source                  1..21
                        mol_type = other DNA
                        organism = synthetic construct
SEQUENCE: 10
gtctggattt gaccgtgctt g                                     21

SEQ ID NO: 11           moltype = DNA  length = 20
FEATURE                 Location/Qualifiers
source                  1..20
                        mol_type = other DNA
                        organism = synthetic construct
SEQUENCE: 11
ggggtcccaa ataccactct                                       20

SEQ ID NO: 12           moltype = DNA  length = 20
FEATURE                 Location/Qualifiers
source                  1..20
                        mol_type = other DNA
                        organism = synthetic construct
SEQUENCE: 12
cttgaacaag ggcagaggag                                       20

SEQ ID NO: 13           moltype = DNA  length = 20
FEATURE                 Location/Qualifiers
source                  1..20
                        mol_type = other DNA
                        organism = synthetic construct
SEQUENCE: 13
ccattgccca aaaacactct                                       20

SEQ ID NO: 14           moltype = DNA  length = 20
FEATURE                 Location/Qualifiers
source                  1..20
                        mol_type = other DNA
                        organism = synthetic construct
SEQUENCE: 14
caacttggtc attcgtggtg                                       20

SEQ ID NO: 15           moltype = DNA  length = 21
FEATURE                 Location/Qualifiers
source                  1..21
                        mol_type = other DNA
                        organism = synthetic construct
SEQUENCE: 15
gtgttgtttg cctcgactga c                                     21

SEQ ID NO: 16           moltype = DNA  length = 21
FEATURE                 Location/Qualifiers
source                  1..21
                        mol_type = other DNA
                        organism = synthetic construct
SEQUENCE: 16
gcaagcaatg ggatgttgac a                                     21

SEQ ID NO: 17           moltype = DNA  length = 21
FEATURE                 Location/Qualifiers
source                  1..21
                        mol_type = other DNA
                        organism = synthetic construct
SEQUENCE: 17
tgcgtctttc tgccagctta a                                     21

SEQ ID NO: 18           moltype = DNA  length = 21
FEATURE                 Location/Qualifiers
source                  1..21
                        mol_type = other DNA
                        organism = synthetic construct
SEQUENCE: 18
tgggtctgca ttatcgccat t                                     21

SEQ ID NO: 19           moltype = DNA  length = 21
FEATURE                 Location/Qualifiers
source                  1..21
                        mol_type = other DNA
                        organism = synthetic construct
```

-continued

```
SEQUENCE: 19
caaacgctca cactcgaatc c                                        21

SEQ ID NO: 20          moltype = DNA  length = 21
FEATURE                Location/Qualifiers
source                 1..21
                       mol_type = other DNA
                       organism = synthetic construct
SEQUENCE: 20
cgcccaaagt gaagttcttc g                                        21

SEQ ID NO: 21          moltype = DNA  length = 21
FEATURE                Location/Qualifiers
source                 1..21
                       mol_type = other DNA
                       organism = synthetic construct
SEQUENCE: 21
tacagatcgg gctatgacgg t                                        21

SEQ ID NO: 22          moltype = DNA  length = 21
FEATURE                Location/Qualifiers
source                 1..21
                       mol_type = other DNA
                       organism = synthetic construct
SEQUENCE: 22
ttgcctctta ccatcccact g                                        21

SEQ ID NO: 23          moltype = DNA  length = 21
FEATURE                Location/Qualifiers
source                 1..21
                       mol_type = other DNA
                       organism = synthetic construct
SEQUENCE: 23
tactctgtgt ggattggtgg c                                        21

SEQ ID NO: 24          moltype = DNA  length = 21
FEATURE                Location/Qualifiers
source                 1..21
                       mol_type = other DNA
                       organism = synthetic construct
SEQUENCE: 24
aacaatcgat ggaccggact c                                        21
```

ANTIFUNGAL QUERCETIN CONJUGATES, METHODS OF PREPARATION AND USES THEREOF

SEQUENCE LISTING

This application includes as the Sequence Listing the complete contents of the accompanying text file "Sequence.txt", created Oct. 3, 2025, containing 2200 bytes, hereby incorporated by reference.

FIELD OF THE INVENTION

The invention generally relates to antifungal agents and methods for use thereof, and in particular to an antifungal agent derived from quercetin. The invention further relates to methods for the treatment of drug-resistant fungal infections, including those caused by *Candida* auris.

BACKGROUND

Antimicrobial resistance is a growing global health threat, with resistance observed across nearly all classes of antimicrobial agents. In response, the World Health Organization (WHO) has introduced the AWaRe classification, listing over 200 antibiotic molecules and formulations to promote their responsible use and preserve their clinical efficacy.

Among the most concerning challenges is the rise in drug-resistant fungal infections. Fungal pathogens affect over a billion people globally, leading to an estimated 11.5 million serious infections and more than 1.5 million deaths each year. Invasive fungal infections in particular are associated with alarmingly high mortality rates-often exceeding 50%-despite the availability of antifungal therapies. This underscores the urgent need for the development of new and effective antifungal agents capable of combating resistant fungal strains.

Quercetin is a naturally occurring flavonoid widely recognized for its antioxidant, anti-inflammatory, and antimicrobial properties. However, its clinical potential, particularly as an antifungal agent, is limited due to poor water solubility, rapid metabolism, and low bioavailability.

Some articles describing the use of quercetin to treat fungal infections include *Journal of Obstetrics, Gynecology and Cancer Research* 2025, 10 (2): 127-144*; Phytomedicine* 114 (2023) 154800*; Molecules* 27 (2022) 2494*; International Immunopharmacology* 93 (2021) 107435*; Fungal Biology* 124 (2020) 83-90*; Journal de Mycologie Médicale* 30 (2020) 101014*; Biofouling,* 35 (3), 320-328*; Cellular Physiology and Biochemistry* 40 (2016) 727-742 and Medicinal Chemistry Research 21 (2012) 2217-2222.

Several patents discuss the use of quercetin in different compositions for enhancing physical or mental performance or treating various diseases or disorders. For example, U.S. Pat. No. 8,440,704B2 to Thomas Christian Lines, describes a preparation method of genipin-crosslinked quercetin-zein/pectin/chitosan nanoparticles, and Jia Chengsheng et al. in CN114098076B as similar technology. A quercetin drug-loading system based on copper sulfide-metal organic framework material is described in Luan Yuxia et al. in CN108524935B.

The World Health Organization (WHO) notes that fungal pathogens are a major threat to public health as they are becoming "increasingly common and resistant to treatment with only four classes of antifungal medicines currently available", and few candidates are in the clinical pipeline. Up to 95% of all invasive *Candida* infections in the United States are caused by non-*albicans Candida* species. Although C. *albicans* is still the leading cause of candidemia, increasing proportions of cases in recent years have been attributed to non-*albicans* species, that are resistant to antifungal drugs. *C. auris* is an emerging multidrug-resistant fungal pathogen that is associated with nosocomial infections and presents a serious global health threat.

Centers for Disease Control (CDC) is concerned about this pathogen because it is often multi-drug resistant, is difficult to identify using standard laboratory methods, and has caused outbreaks in healthcare settings. In the United States, about 90% of *C. auris* isolates have been resistant to fluconazole, about 30% have been resistant to amphotericin B, and around 5% have been resistant to echinocandins. Therefore, urgent and serious steps need to be taken to prevent outbreaks that could prove devastating.

Additionally, systemic candidiasis is linked with a high rate of mortality in immunocompromised individuals. In the past few years, the escalating use of drugs for the treatment of *Candida* infections ranging from superficial to invasive has resulted in the emergence of drug-resistant strains of *Candida*. Therefore, the development of a potential anti-*Candida* agent with lesser toxicities has become a high priority in the field. Moreover, individuals suffering from conditions such as HIV/AIDS, organ transplantation, and chemotherapy are expected to rise over the next ten years and these patients are susceptible to *Candida* infections with serious side effects. Thus, the requirement for a novel anti-*Candida* agent with targeted action is increasing.

The emergence of multi-drug-resistant *Candida* strains has been widely reported in the past few years, and it is well demonstrated that these resistant phenotypes can emerge over the period of infection and even in response to the treatment process, which poses an additional threat to the sick patients. Furthermore, these infections put a significant economic burden on the individual Despite increasing numbers of health-compromised people, who are prone to life-threatening fungal infection, only four classes of antifungal drugs are approved by the US Food and Drug Administration (FDA) for treating infections caused by *Candida* species. These drugs include polyenes, azoles, echinocandins, and flucytosine. Although current medications could prevent infections, a problem arises when the microbes develop resistance to different defense mechanisms.

The polyene class of antifungals are associated with dose-related toxicity, mainly nephrotoxicity, however, the discovery of lipid formulations has lowered the risk factors. Further, and of more importance, increasing drug resistance is an unavoidable problem. The reduction of fluconazole susceptibility in some *candida* strains, especially *C. auris*, is becoming a challenge for HIV patients, although second-generation antifungals (triazole agents and echinocandins) have addressed some issues. However, treatment failures and the advent of resistance against echinocandin antifungal agents have been reported and therefore, the mortality rates for candidemia remain high. This situation thus emphasizes the pressing need for more effective and less toxic antifungal agents against *C. auris* infection.

Conjugation of bioactive molecules to biocompatible carriers is an established strategy in pharmaceutical development to enhance drug solubility, stability, targeted delivery, and systemic circulation time. In the context of antifungal therapy, this approach is particularly valuable for improving the clinical utility of compounds with limited pharmacokinetic profiles. Quercetin, a naturally occurring flavonoid, exhibits broad-spectrum antimicrobial activity, including activity against fungal pathogens. However, its therapeutic application is constrained by poor water solubility, rapid metabolism, and low bioavailability. Although strategies such as fluorine substitution, co-administration with antifungal agents like fluconazole, and incorporation into nanocarrier systems have shown promise, these approaches offer limited control over targeted delivery and sustained release.

SUMMARY

Considering the disadvantages of the prior art, the following summary is provided to facilitate an understanding of some of the innovative features unique to the present invention and is not intended to be a full description. A full appreciation of the various aspects of the invention can be gained by taking the entire specifications, claims, drawings, and abstract as a whole.

In one embodiment, the invention is an antifungal agent derived from quercetin. In another embodiment, the invention is a pharmaceutical composition comprising a quercetin derivative conjugate having antifungal properties. In another embodiment, the invention is a quercetin derivative conjugate conjugated to a biocompatible molecule selected from the group consisting of a polymer, a polysaccharide, a protein and a peptide.

In another embodiment, the invention is a method for the treatment of drug-resistant fungal infection using the pharmaceutical composition comprising the quercetin derivative. In another embodiment, the invention is a method of inhibiting a fungal infection in a subject at risk thereof, comprising administering to the subject a prophylactically effective amount of the quercetin derivative conjugate. In one embodiment, the fungal infection is a drug-resistant fungal infection. Thus, fungus may be resistant to at least one antifungal agent, including but not limited to a polyene, an azole, an echinocandin, a flucytosine and Amphotericin B.

In one embodiment, the fungus is a *Candida* species, and in particular, the *Candida* species may be *Candida* auris. The method comprises contacting the fungus with a therapeutically effective amount of the quercetin derivative conjugate.

In yet another embodiment, the pharmaceutical composition comprises a pharmaceutically acceptable carrier, excipient, or diluent, and is formulated for administration via a route including but not limited to oral, topical, intravenous, or inhalation.

In one embodiment, the invention is a method of chemically conjugating quercetin via a cystamine linker to guar gum, which is a biodegradable and biocompatible polysaccharide. The cystamine linker introduces a redox-responsive disulfide bond, enabling intracellular cleavage and controlled release of the active agent. This novel conjugate has improved physicochemical properties and enhanced antifungal efficacy, particularly against drug-resistant strains such as *Candida auris.*

In particular, compositions comprising a derivative/conjugate of the invention are formulated to control and combat infections caused by resistant *C. auris* in immunocompromised patients. An exemplary derivative/conjugate is a guar gum cys-quercetin conjugate (GGQC1) having the following structural formula:

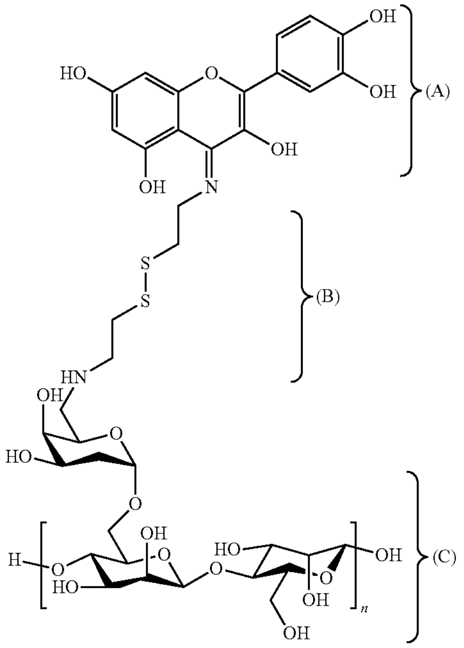

wherein

A is quercetin;

B is a cystamine linker; and

C is guar gum.

In one embodiment, the invention is a method of preparing the GGQC1. Additional features and advantages of the present invention will be set forth in the description of disclosure that follows, and in part, will be apparent from the description of may be learned by practice of the disclosure. The disclosure will be realized and attained by the compositions and methods particularly pointed out in the written description and claims hereof.

BRIEF DESCRIPTION OF THE DRAWINGS

The patent or application file contains at least one drawing executed in color. Copies of this patent or patent application publication with color drawings will be provided by the Office upon request and payment of the necessary fee.

The accompanying drawings, which are incorporated in and constitute a part of this specification, illustrate embodiments of the invention and, together with a general description of the invention given above, and the detailed description given below, serve to explain the invention.

(FIG. 10A) The detection of DCFH-DA was done by fluorescence microscopy. Whereas no ROS production with zero fluorescence was recorded in the negative control, ROS production was detected in the positive control ($H_2O_2$-treated) and test compound (MIC) treated *C. auris* strains, as evident with enhanced green fluorescence. (FIG. 10B) The mean fluorescence intensity of DCFH-DA after treatment with different concentrations of the test compound.

DETAILED DESCRIPTION

Figure 1:
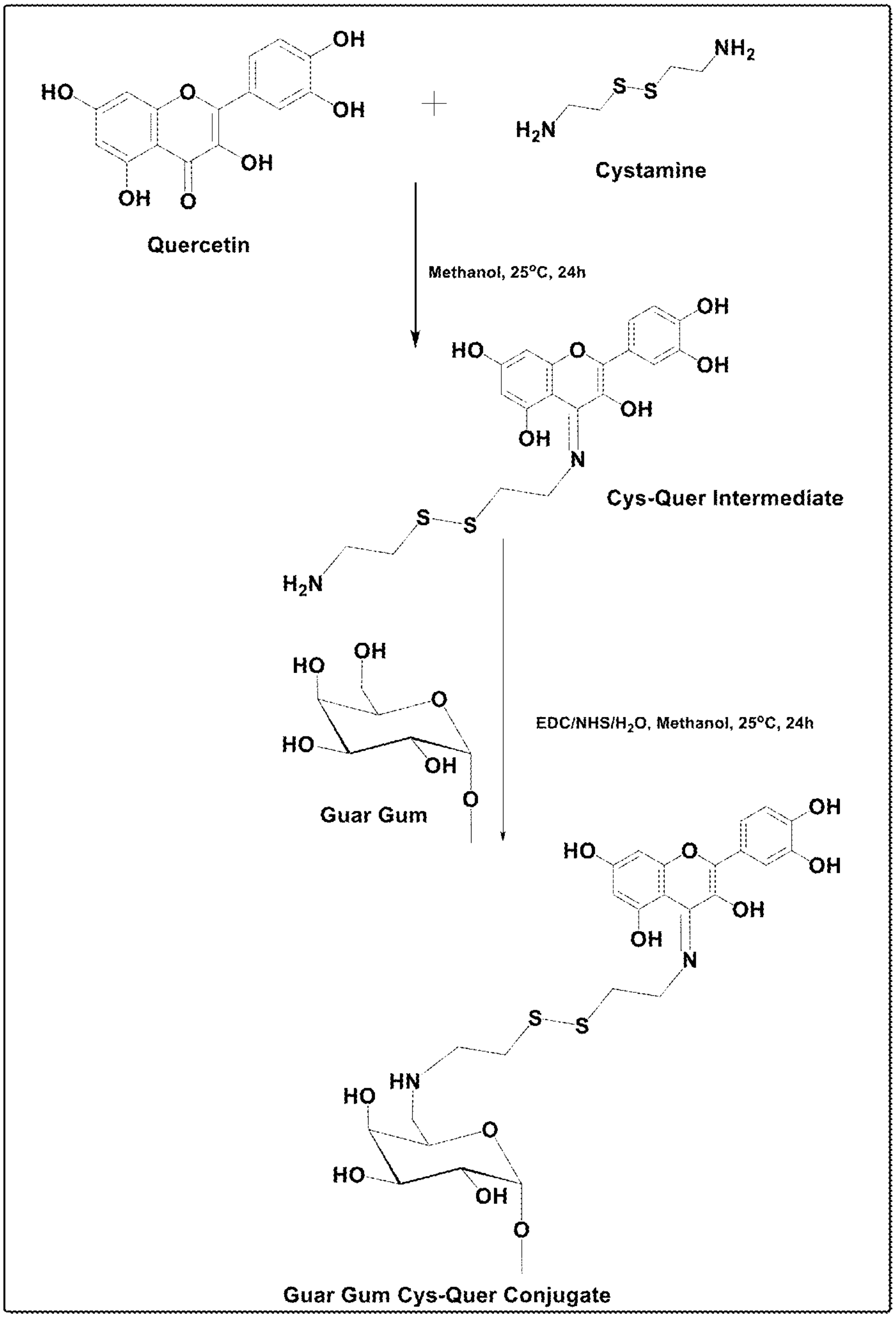
FIG. 1 is a schematic of the synthesis of guar gum Cys-Quercetin Conjugate (GGQC1).

Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure, or manner.

In general, embodiments of the invention comprise molecules that have antifungal activity against drug resistant *C. auris*. In one embodiment of the invention, quercetin was conjugated with guar gum, a biocompatible and biodegradable polysaccharide known for its mucoadhesive and controlled-release properties. A cystamine linker was employed to bridge quercetin and guar gum, enabling site-specific release through reductive cleavage in the intracellular environment of fungal cells. This strategic conjugation not only improves the solubility and stability of quercetin but also facilitates targeted and sustained delivery, thus overcoming the limitations of the prior art and resulting in enhanced antifungal activity against drug-resistant strains such as *Candida auris*.

An exemplary derivative/conjugate is a guar gum cys-quercetin conjugate (GGQC1) having the following structural formula:

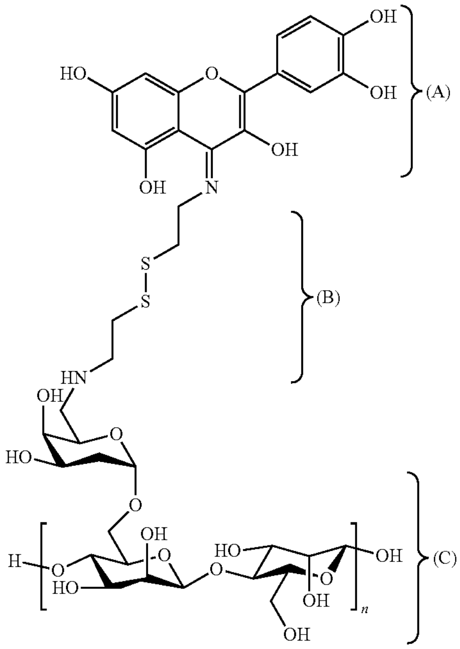

wherein

A is quercetin;

B is a cystamine linker; and

C is guar gum.

In one embodiment, the invention includes a method of preparing the GGQC1.

As will be demonstrated in examples of the invention, the GGQC1 exerted fungicidal activity which was concentration- and time-dependent (defined as a kill of ≥log 3) against test *C. auris* strain. The median value of 2 times MIC was responsible for causing candidacidal endpoint after 12 h whereas, 4 times MIC resulted in candidacidal endpoint after 24 h. The average $\log_{10}$ CFU/mL for healthy control was 7.78 which was reduced to 5.8 after 24 hr exposure to ½ MIC and 4.67 after 24 hr of exposure to MIC. Furthermore, after treating with the MIC value of ICP8 a 50% reduction in the $\log_{10}$ CFU/mL from the inoculum was observed after 12 h, however, with the increasing concentration, two and four times the MIC value, the 50% reduction in the number of CFU was achieved after 4 and 2 h respectively. The results obtained from the time-kill curve showed that ICP8 killed the *C. auris* strain at concentrations above the MIC value and further confirmed that the compound is fungicidal in nature.

Fractional inhibitory concentrations (ΣFIC), which in turn signifies the nature of the interaction between ionic liquids and amphotericin B, showed synergistic (ΣFIC≤0.5), additive (ΣFIC>0.5-≤1) and no interaction (ΣFIC>1-<2) combinations of the ionic liquids and amphotericin B for tested *C. auris* strain. A four-fold decrease in the MIC of ionic liquid ICP8 as well as amphotericin B was observed, when used together. Therefore, the MIC value of ICP8 and amphotericin B was significantly reduced when used in combination.

Embodiments of the invention provide a pharmaceutical composition comprising a quercetin guar gum conjugate/quercetin derivative and a pharmaceutically acceptable carrier. The conjugate comprises of quercetin and guar gum linked through a cystamine linker.

As used herein, the terms "pharmaceutical", "pharmaceutical composition" and "pharmaceutically acceptable" are used interchangeably to refer to molecular entities and compositions that do not produce an adverse, allergic, or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In some embodiments, guar gum may be replaced by another biocompatible polymer, polysaccharide, protein or peptide, including but not limited to alginate, chitosan, dextran, hyaluronic acid, gelatin, collagen, polyethylene glycol (PEG), polyvinyl alcohol (PVA), polylactic acid (PLA), polyglycolic acid (PGA), poly(lactic-co-glycolic acid) (PLGA).

In some embodiments, the linker may be any cleavable linker. Examples include but are not limited to a peptide linker, disulfide linkers, ester linkers, hydrazone linkers, or carbamate linkers. Cleaving agents may include chemical or enzymatic agents, such as proteases (e.g., trypsin or cathepsin B), esterases, reducing agents (e.g., glutathione), or acidic conditions.

Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. Other suitable excipients include, for example, an inert diluent such as lactose, granulating and disintegrating agents such as cornstarch, binding agents such as starch, and lubricating agents such as magnesium stearate.

In another embodiment of the invention, the excipient in the composition is an additive, solvent, oil, emulsifier, surfactant, stabilizer, cooling agent, preservative, antioxidant, gelling agent, moisturizing agent, emollient, penetration enhancer, colorant, fragrance, pH modifier, conditioning agent, pearlizing agent, skin barrier repair agent, and/or combinations thereof.

The composition may contain any such additional ingredients so as to provide the composition in a form suitable for administration. The final amount of compound in the formulations may vary. However, in general, the amount in the formulations will be from about 1% to about 99%. In some embodiments, the amount of the compound in the formulations is from about 10% to 90%, 20% to 80%, 1% to 25%, 5% to 20%, 10% to 15%, 0.5-2% or 2-5%.

In some embodiments, the composition is an oily solution or suspension. In some embodiments, the formulation is in a solid dosage form, such as a tablet, dragee, capsule, caplet or gelcap.

In some embodiments, the composition is employed for the purpose of topical and/or local administration in the form of oils, creams, lotions, serums, gels, ointments, foams, sprays, aerosols, coating on implants, silicon tubes, catheters, sutures and the like.

In some embodiments, the composition comprises one or more additional antifungal agents. Suitable antifungal agents include but are not limited to allylamines, benzylamines, azoles, polyenes, echinocandins, N-hydroxy pyridone, N-hydroxy pyrithione, tavaborole, flucytosine, griseofulvin, hinokitol and combinations thereof. In some embodiments, the N-hydroxy pyridone is piroctone olamine, ciclopirox olamine or a combination thereof; the N-hydroxy pyrithione is zinc pyrithione or any respective bivalent metal coordinating complexes or combinations thereof; allylamines may include terbinafine, amorolfine, naftifine and combinations thereof; the benzylamine is butenafine; the azoles are imidazoles, triazoles or thiazoles may include ketoconazole, climbazole, miconazole nitrate, fluconazole, econazole, saperconazole, oxiconazole, clotrimazole, bifonazole, butoconazole, fenticonazole, isoconazole, omoconazole, sertaconazole, sulconazole, tioconazole, luliconazole, chlormidazole, croconazole, eberconazole, omoconazole, isoconazole, neticonazole, albaconazole, efinaconazole, fosfluconazole, epoxiconazole, fluconazole, isavuconazole, itraconazole, posaconazole, propiconazole, ravuconazole, terconazole, voriconazole, hexaconazole, abafungin and combinations thereof; the polyenes may include natamycin, nystatin and combinations thereof; and the echinocandins may include caspofungin, anidulafungin, micafungin and combinations thereof.

Embodiments of the invention further provide methods of inhibiting growth of a fungus comprising contacting the fungus with an effective amount of the Quercetin conjugate as described herein. In some embodiments, the method is for treating a fungal infection in a subject in need thereof or managing fungal growth, comprising administering the conjugate alone or in combination with other antifungals or pharmaceutical composition thereof described herein to the subject.

In one embodiment of the invention, the method of treating or managing comprises inhibiting the fungal growth, reducing the fungal growth, eliminating the fungus, curing drug resistant fungal infections, treatment of fungal infections in clinical non-responders and patients with barrier defects, or any combination thereof. In another embodiment, the treatment described herein includes medical treatment, cosmetic treatment, or a combination thereof.

The methods and uses described herein may further include treating a subject in need thereof, comprising the steps of administering the conjugate or composition in an oral delivery vehicle, food product, nutritional supplement, dietary supplement, or functional food comprising the formulation to the subject. In some embodiments, the administration is oral, topical, parenteral, enteral, transdermal, intradermal, intraocular, intravitreal, sublingual, or intravaginal, and may preferably comprise an effective amount of the conjugate or composition.

In some embodiments, the composition is administered concomitantly or sequentially with one or more additional antifungal agents as described herein.

A patient or subject to be treated by any of the compositions or methods of the present disclosure can mean either a human or a non-human animal including but not limited to dogs, horses, cats, rabbits, gerbils, hamsters, rodents, birds, aquatic mammals, cattle, pigs, camelids, and other zoological animals.

In some embodiments, the fungal infection or fungal growth is caused by fungi including *Candida* species, *Malassezia* species, *Trichophyton* species, *Microsporum* species, *Epidermophyton* species, *Aspergillus* species, *Cryptococcus* species and combinations thereof.

In another embodiment of the present disclosure, the fungal infection or fungal growth is caused by *Candida* spp., including *C. auris, C. albicans, C. glabrata, C. guilliermondii, C. krusei, C. lusitaniae, C. parapsilosis, C. tropicalis, C. colliculosa, C. dubliniensis, C. famata, C. haemulonii, C. inconspicua, C. intermedia, C. kefyr, C. lipolytica, C.* metapsilosis, *C. norvegensis, C. orthopsilosis, C. pelliculosa, C. pulcherrima, C. nrugose, C. utilis, C. viswanathii*, and *C. zeylanoides; Malassezia* spp. selected from the group consisting of *M. furfur, M. pachydermatis, M. globosa, M. restricta, M. sloofiae, M. sympodialis, M. nana, M. yamatoensis, M. dermatis, M. obtusa, M. japonica, M. caprae, M. cuniculi, M. equine*, and *M. arunalokei; Trichophyton* spp. selected from the group consisting of *T. rubrum, T. mentagrophyte, T. interdigitale, T. tonsurans, T. schoenleinii, T. violaceum, T. abissinicum, T. balcaneum, T. circonvolutum, T. concentricum, T. eboreum, T. errinacei, T. fischeri, T. fluviomuniense, T. glabrum, T. gourvilii, T. kanei, T. kuryangei, T. megninii, T. pedis, T. proliferans, T. raubitschekii, T. redellii, T. rodhainii, T. simii, T. soudanense, T. thuringiense, T. verrucosum, T. violaceum* and *Trichophyton yaoundei; Microsporum* spp. including *M. audouinii, M. canis*, M. amazonicum, M. boullardii, M. cookie, M, *distortum, M. duboisii, M equinum, M. ferrugineum, M. fulvum, M. gallinae, M. gypseum, M. langeronii, M. nanum, M. persicolor, M. praecox, M. ripariae* and *M. rivalieri; Epidermaphyton* spp such as *E. floccosum*; and other non-dermatophytes including but not limited to *Aspergillus* spp. such as *A. fumigates, A. flavus, A. nidulans, A. terreus, A. lentulus, A. niger, A. alliaceus, A. arvii, A. brevipes, A. calidoustus, A. conjunctus, A. deflectus, A. duricaulis, A. emericella, A. fischerian, A. fumigatiaffinis, A. fumisvnnematus, A. granulosus, A. novofumigatus, A. panamensis, A. quadrilineatus, A. udagawae, A. unilateralis* and *A. ustus*, and *Cryptococcus* spp. such as $_{C.}$ *neoformans, C. gattii, C. albidus, C. bacillisporus, C. decagatti, C. deuterogatti, C. laurentii, C. tetragatti* and *C. uniguttulatus*; or any combination of fungi thereof.

In some embodiments, the fungus is resistant or susceptible to an anti-fungal agent as described herein. Without wishing to be bound by a theory, the compositions described herein are particularly useful for treatment of fungal infections which are resistant to one or more conventional drugs used for treatment of fungal infections. For example, the compositions of the invention are particularly useful for treatment of fungal infections which are resistant to azoles (e.g. fluconazole), allylamines, benzylamines or amphotericin B.

As used herein, the terms “manage”, “managing”, “management”, “treat”, “treating” or “treatment” of fungus growth or fungus infection refers to both medical or non-medical indications. In one aspect, these terms cover one or more aspects including but not limiting to preventing or reducing growth of fungi, inhibiting further growth of fungi, eliminating the grown fungi at the infected area/site, providing symptomatic relief to a subject in need thereof, successfully eliminating the infection, curing the fungal infection, preventing recurrence of fungal infection, curing drug resistant fungal infections, and treatment of fungal infections in clinical non-responders and patients with barrier defects.

In some embodiments, the composition is administered to the subject in a therapeutically effective amount. By a “therapeutically effective amount” is meant a sufficient amount of active agent to treat the disease or disorder at a reasonable benefit/risk ratio applicable to any medical treatment (e.g., sufficient to kill the fungal infection, halt the progression of the fungal infection, and/or to reduce some or all of the adverse symptoms caused by the fungal invention). It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250, 500, and 1,000 mg of the active ingredient for the symptomatic adjustment of the dosage to the subject to be treated. An effective amount of the drug is ordinarily supplied at a dosage level from 0.0002 mg/kg to about 20 mg/kg of body weight per day, especially from about 0.001 mg/kg to 7 mg/kg of body weight per day. In some embodiments, the composition is administered daily or 2, 3, 4, 5, 6, 7, or more times weekly. It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms “a”, “an”, and “the” include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order, which is logically possible.

Examples of the Invention

Methods

As shown in FIG. 1, quercetin (500 mg) was dissolved in 50 mL of methanol at 25° C. under stirring. After stirring for 30 min, cystamine (500 mg) that was also dissolved in 50 ml in methanol was introduced into the quercetin solution, and then the reaction mixture was stirred at 25° C. for about 24 h and the product was obtained by evaporating the solvent using rotatory evaporator. Later, guar gum (500 mg) was dissolved in 250 ml water for 24 hours to make it completely soluble. After 24 hours EDC/NHS solution was added to the guar gum solution which was prepared in 50 mL of distilled water using 300 mg and 200 mg of EDC and NHS respectively. The quercetin-cystamine derivative was introduced into this guar gum solution dropwise and the reaction mixture was stirred for 24 hours at 25° C. as shown in FIG. 1.

In this example, the antifungal activity of the conjugate against *C. auris* was investigated in terms of minimum inhibitory concentration (MIC) and minimum fungicidal concentration (MFC). The frozen stocks of five different *C. auris* strains were propagated onto Sabouraud dextrose agar (SDA; Merck, Germany) plates for 72 h at 35±2° C. The primary inoculum of *C. auris* was grown in SD Broth (Merck, Germany) at 35±2° C., 200 rpm for 24 h. Later, the broth was centrifuged, and the pellet was resuspended in the desired growth media to obtain a cell density of $1.0\text{-}5.0\times10^6$ CFU/mL (0.5 McFarland Standard) using a turbidity meter.

The minimum inhibitory concentration (MIC) values for the compound were estimated using the guidelines provided by the Clinical and Laboratory Standards Institute (CLSI) (Clinical and Laboratory Standards Institute. 2017 CLSI). All five strains of *C. auris* were propagated in RPMI medium, buffered with morpholine propanesulfonic acid (MOPS) to pH 7.0. The compound was dissolved in 1% DMSO to prepare a 1 mg/mL stock. The stock was serially diluted in a 96-well plate to achieve concentrations ranging from 125 to 0.004 μg/mL. Similarly, caspofungin, the positive control, was serially diluted to achieve a concentration from 62.5 to 0.002 μg/ml in a 96-well plate. The yeast inoculum was prepared as recommended by CLSI (Clinical and Laboratory Standards Institute. 2017) and the plates were incubated at 35±2° C. at the static condition for 48 h. After incubation, the absorbance was measured at 450 nm. The MIC90 was confirmed as the lowest concentration of the compound, inhibiting ≥90% of yeast growth. The test compound's minimum fungicidal concentration (MFC) was determined in parallel against all *C. auris* strains. Briefly, all the wells showing no growth were sub-cultured on SDA plates and incubated for 24 h at 35±2° C. The lowest concentration without any growth was recorded as MFC.

The yeast strains were suspended in SD broth at a density of $1.0\text{-}5.0\times10^6$ CFU/mL, then diluted 1/10 ($1.0\text{-}5.0\times10^5$ CFU/mL, to obtain a working concentration of $0.5\text{-}2.5\times10^5$ CFU/mL). All the *C. auris* strains under investigation were co-incubated with test compounds at their MFCs. The yeast cells incubated only with SDB were used as a negative control. The experimental setup was incubated at 35±2° C., 200 rpm, for 24 h, and the sample was collected at various time points (0 h, 2 h, 4 h, 8 h, 12 h, and 24 h). To determine the viable count, 1/10 serial dilutions were prepared, and 50 μL of each dilution was plated onto SDA plates and incubated at 35±2° C. for 24 h. The colonies were counted, the CFU/mL values were calculated, and a time-kill curve was plotted.

2,7-dichlorofluorescein diacetate (DCFH-DA) was used to detect the ROS levels in the *C. auris* strain. The rationale behind using this method is that the oxidation of DCFH-DA to 2'-7' dichlorofluorescein (DCF) is widely used for detecting total ROS, including hydroxyl radicals (·OH) and nitrogen dioxide ($\cdot NO_2$). Mechanistically, DCFH-DA enters the cells, where intracellular esterases remove the acetyl groups, generating the non-fluorescent DCFH. Upon oxidation by ROS, DCFH is converted into DCF, which emits green fluorescence with an excitation wavelength of 485 nm and an emission wavelength of 530 nm. The yeast cells (0.5 McFarland standard) were exposed with or without the test compound (MIC and MFC) for 4 h at 35±2° C., 200 rpm. Then, the cells were collected, washed three times with PBS, and stained with DCFH-DA (10 μM) at 37° C. for 30 min in a dark room. Thereafter, the cells were centrifuged (5000 rpm, 10 minutes) and resuspended in PBS; 100 μL of resuspended cells were transferred to a black 96-well plate, and the fluorescence intensity (Ex/Em=485 nm/530 nm) was measured using a fluorescence microplate reader. The $H_2O_2$ (15 mM) treated *C. auris* cells were used as a positive control.

To acquire the total RNA content of *C. auris* with or without treatment with the test compound (MFC), 0.5 McFarland standard was grown at 35±2° C. and 200 rpm in SD broth for 4 h. The cells were centrifuged at 10,000 g at 4° C. for 10 minutes, and the pellet was washed with cold PBS. The total RNA was extracted following Zymo Research Quick-RNA Fungal/Bacterial Miniprep Kit (Zymo Research Corp) guidelines. The concentration of RNA was verified with the help of a NanoDrop spectrophotometer. The gene expression analysis of crucial *C. auris* oxidative stress genes (CAT1, SOD1, SOD2, SOD4, SOD6, TSA1B, GPX2, SSK1, GST1, GSHR, and CCP1) that are homologous to the genes explained to be important for oxidative stress response in *C. albicans* was performed. The obtained total RNA samples were converted to cDNA with iScript™ cDNA Synthesis Kit (Bio-Rad) and analyzed as described elsewhere. The list of primers used for the study is mentioned in Table 1. The fold change (FC) values relative to the *C. auris* housekeeping gene (ACTI) were calculated by the Livak method ($2^{-1\Delta\Delta Cq}$).

TABLE 1

Primers used for gene expression analysis.

| Gene | Forward primer (5' > 3') | SEQ ID NO | Reverse primer (5' > 3') | SEQ ID NO |
|---|---|---|---|---|
| CAT1+ | GTCATCTTGTTCTCCGACCGT | 1 | CCAGTTGCCGTCCTTTGTAGA | 2 |
| SOD1+ | TTGGCAGATCTGTGGTTGTCC | 3 | GACGCCAATAACACCACAAGC | 4 |
| SOD2 nothing | GGTGGTGCTTTGGATGTTGTC | 5 | CAAGTAGTAAGCGTGCTCCCA | 6 |
| SOD4+ | TCAACCCTTACCACGGCTAC | 7 | CACCACCACAGACAAGTTGG | 8 |
| SOD6+ | ATCTTCAACCCTTACCACGCC | 9 | GTCTGGATTTGACCGTGCTTG | 10 |
| GST1- | GGGGTCCCAAATACCACTCT | 11 | CTTGAACAAGGGCAGAGGAG | 12 |
| GSHR- | CCATTGCCCAAAAACACTCT | 13 | CAACTTGGTCATTCGTGGTG | 14 |
| TSA1B+ | GTGTTGTTTGCCTCGACTGAC | 15 | GCAAGCAATGGGATGTTGACA | 16 |
| GPX2- | TGCGTCTTTCTGCCAGCTTAA | 17 | TGGGTCTGCATTATCGCCATT | 18 |
| SSK1 nothing | CAAACGCTCACACTCGAATCC | 19 | CGCCCAAAGTGAAGTTCTTCG | 20 |
| CCP1+ | TACAGATCGGGCTATGACGGT | 21 | TTGCCTCTTACCATCCCACTG | 22 |
| ACT1 | TACTCTGTGTGGATTGGTGGC | 23 | AACAATCGATGGACCGGACTC | 24 |

Annexin V-FITC apoptosis detection kit was used to classify early/late cellular apoptosis in the cells treated with the test compound. Briefly, the yeast cells (0.5 McFarland standard) were exposed with or without (control) the test compound for 4 h at 35±2° C., 200 rpm. Then, the cells were collected and washed three times with PBS. For protoplast preparation, *C. auris* cells were treated with snailase (2%) for 2 h at 30° C. resulting in the removal of cell walls. Then, the cells were spun, washed thrice with sorbitol (1.2 M), and resuspended in binding buffer (1.2 M sorbitol, 0.05 M tris base, 0.01 M $MgCl_2$, pH 7.4). The cellular integrity and externalization of phosphatidylserine (PS) protoplasts of *C. auris* cells were stained with annexin V-FITC Apoptosis Detection Kit I (BD, USA) for 15 min in the dark. Next, the induction of apoptosis was determined by flow cytometer (BD, USA) with a total of 10,000 events counted at the flow rate. FlowJo™ v10 software (BD, USA), was used to analyze the flow data.

Mitochondrial membrane potential (MMP), a key indicator of early cellular apoptosis, was assessed using 5,5',6,6'-tetrachloro-1,1',3,3'-tetraethyl-benzimidazolyl-carbocyanine iodide (JC-1; Biotium) by monitoring the shift from red to green fluorescence. The *C. auris* cells (0.5 McFarland standard) were exposed with or without the test compound (MIC and MFC) for 4 h at 35±2° C., 200 rpm. Then, the cells were collected and washed three times with PBS and stained with JC-1 dye (2.5 µg/mL) for 30 minutes in the dark. Again, the cells were washed thrice with PBS, transferred to a black 96-well plate, and analyzed using a fluorescence spectrophotometer. The mitochondrial membrane potential was determined by calculating the ratio of fluorescence intensities of JC-1 aggregates (Ex/Em=540/590 nm) to JC-1 monomers (Ex/Em=490/530 nm).

The L-929 cells were used to determine the cytotoxicity of the test compound following standard protocol. Briefly, cells were propagated in RPMI 1640 medium supplemented with 5% fetal calf serum (FCS) in a humidified chamber of 5% $CO_2$ in air at 37° C. and passaged every 3 or 4 days. The in vitro cytotoxicity of the test compound was estimated by Cell Counting Kit 8 (CCK-8) (Abcam) assay. L929 cells were seeded into 24-well plates at a density of $1.5 \times 10^3$ cells per well, with and without test compound (0.5×MIC, MIC, MFC, 2×MFC, and 4×MFC). The wells containing no test compound served as the negative control. The plates were then incubated at 37° C. with 5% $CO_2$ for 0, 24, and 48 h. Following incubation, the supernatants were removed, and CCK-8 solution (200 µL) was added to each well and incubated for 3 h at 37° C. Then, 200 µL of the sample from each group was transferred to a fresh 96-well plate, and the absorbance was then measured at 450 nm using a microplate reader. The cell viability was calculated using the following equation:

$$\% \text{ Cell viability} = \frac{(OD450 \text{ Sample} - OD450 \text{ Blank})}{(OD450 \text{ Negative control} - OD450 \text{ Blank})} \times 100\%$$

Statistical analysis for all the experiments was performed in triplicate and final outcomes were analyzed by GraphPad Prism® using two-way ANOVA test. Statistical significance was calculated in terms of p value (*$p < 0.001$, $p < 0.01$ and *$p < 0.1$).

Results

Characterization of the Compounds

The covalent conjugation reaction between quercetin and cystamine involves the amine group ($-NH_2$) of cystamine functioning as a nucleophile, which subsequently reacts with the carbonyl carbon (C=O) of quercetin. The dehydration process yields an intermediate that ultimately leads to the development of an amide bond. This interaction facilitates the formation of the intermediate that significantly enhances the stability and solubility of quercetin, a flavonoid well-known for its antioxidant properties, which typically exhibits low bioavailability in its free state. The interaction between the hydroxyl group of guar gum and the amine group of cystamine involves a nucleophilic attack by the amine on the hydroxyl group, resulting in the formation of an amide bond. This reaction is generally aided by coupling agents like N-(3-dimethylaminopropyl)-N'-ethylcarbodiimide hydrochloride (EDC) and N-hydroxysuccinimide (NHS) to activate the hydroxyl group of guar gum, hence enhancing its reactivity with the amine group of cystamine. This modification is frequently employed to produce customized polysaccharides with enhanced characteristics for diverse applications, such as biomedical, drug delivery systems and tissue engineering.

Figure 2:
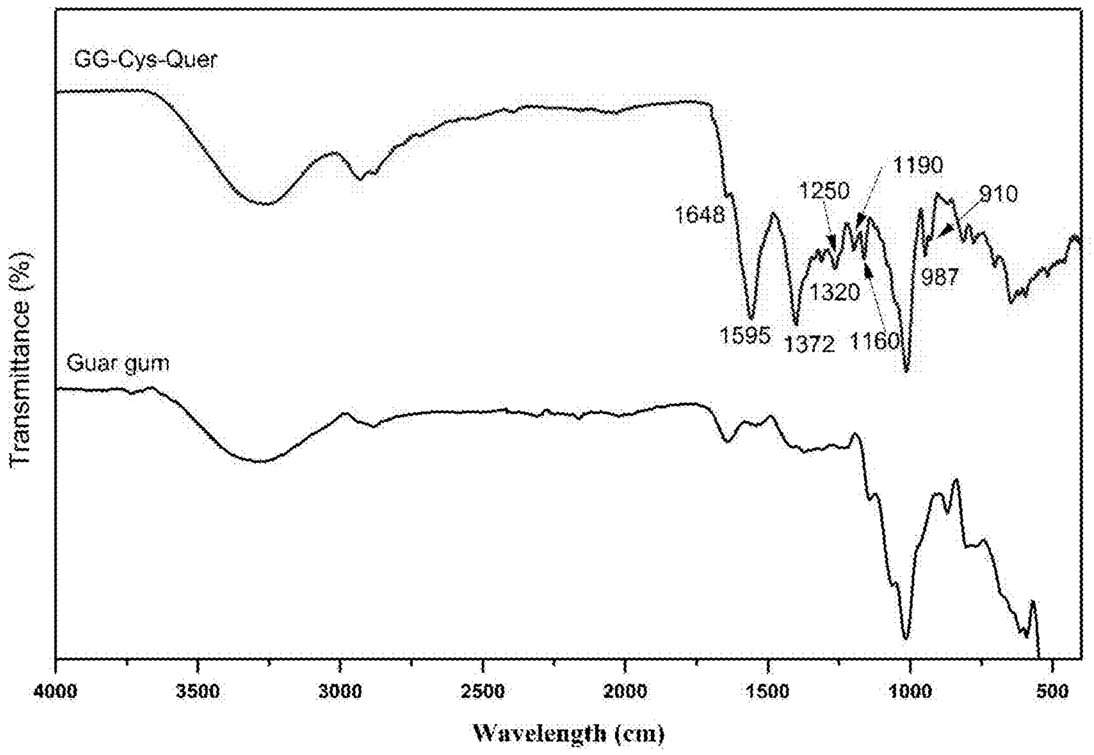
FIG. 2 shows a representative FT-IR spectrum of guar gum and GG-Cys-Quer Conjugate.

Fourier transform infrared analysis facilitates the identification of functional groups by examining the absorption of infrared light across various wavelengths. Guar gum is characterized by its linear chains of mannose and galactose units that branch off in alternating orientations, which contain a significant number of hydroxyl groups. The stretching vibrations of hydroxyl groups (—OH) inherent in the guar gum structure are responsible for the broad peak in the 3200-3500 $cm^{-1}$ range. The C—H stretching vibrations are indicated by peaks at 2800-2900 $cm^{-1}$. The C—O—C stretching vibrations of the glycosidic linkages in the guar gum backbone are represented by a peak at approximately 1371 $cm^{-1}$. In the spectrum of GG-Cys-Quer (FIG. 2) the absorption band of C═C stretching vibration of phenyl ring appears at 1648 $cm^{-1}$. The two peaks at 1372 $cm^{-1}$ and 1320 $cm^{-1}$ correspond to O—H bond bending of the phenol groups. The peaks at 1250 $cm^{-1}$, 1190 $cm^{-1}$, 1160 $cm^{-1}$ corresponds to C═O═C anti-symmetrical stretching and peaks at 987 $cm^{-1}$ and 910 $cm^{-1}$ corresponds to C—O—C symmetrical stretching respectively which arises due to the quercetin.

Figure 3:
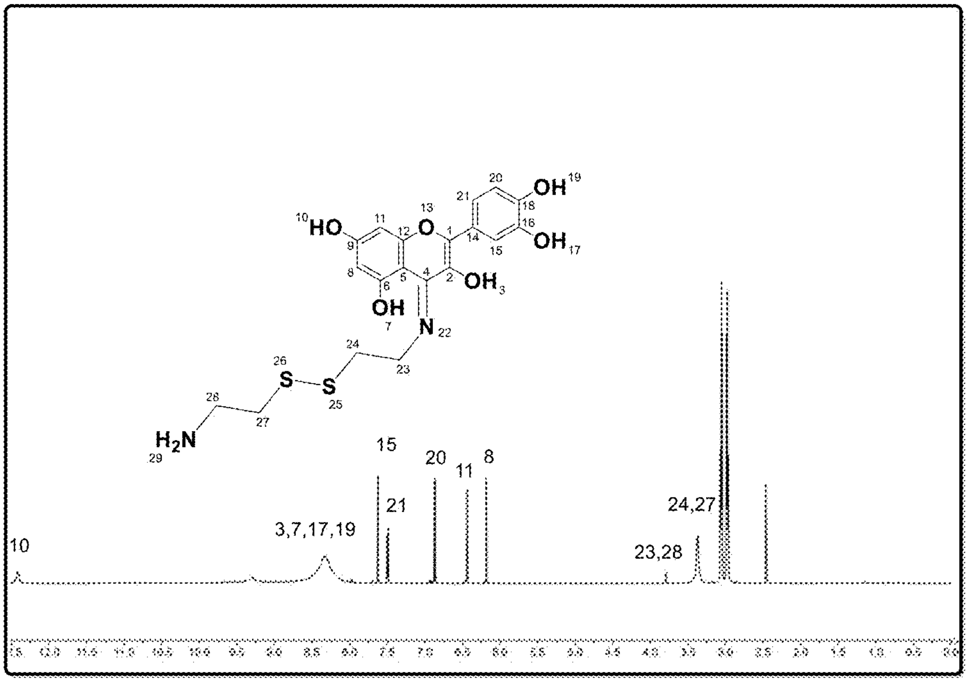
FIG. 3 shows a representative $^{1}$HNMR spectrum of Cys-Quer intermediate.

In the $^{1}$HNMR spectrum of the Cys-Quer intermediate (FIG. 3) the long-range coupling across the aromatic π-system leads the aromatic protons on the benzopyrone ring of quercetin to appear as doublets. The proton resonance peak at δ 12.3 ppm and broad peak at δ 8.3 ppm corresponds to the protons of the hydroxyl groups. The proton peaks corresponding to aromatic region of quercetin were observed at δ 7.6 (C15), 7.5 (C21), 6.8 (C20), 6.5 (C11) and 6.1 (C8) ppm. The peak corresponds to the methylene protons of the cystamine appears at δ 3.7 and 3.3 ppm.

Figure 4:
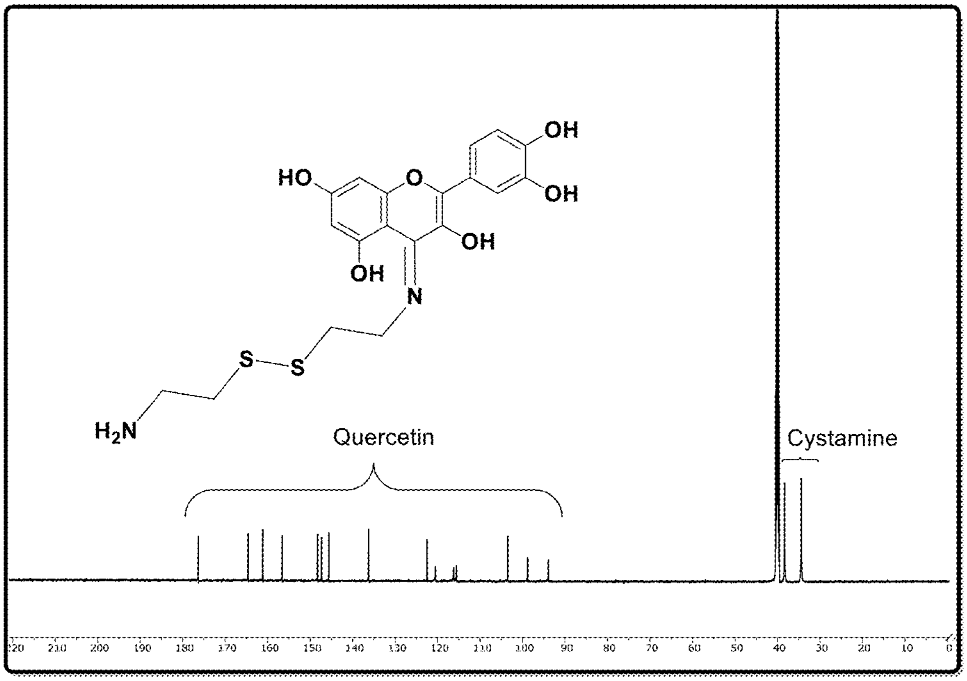
FIG. 4 shows a representative $^{13}$CNMR spectrum of Cys-Quer intermediate.

In the $^{13}$C NMR spectrum of the Cys-Quer intermediate (FIG. 4) the peaks corresponding to carbons of quercetin appears at δ 176.34 to 93.95 ppm whereas the peaks corresponding to cystamine appears at δ 38.33 and 34.41 ppm.

Figure 5:
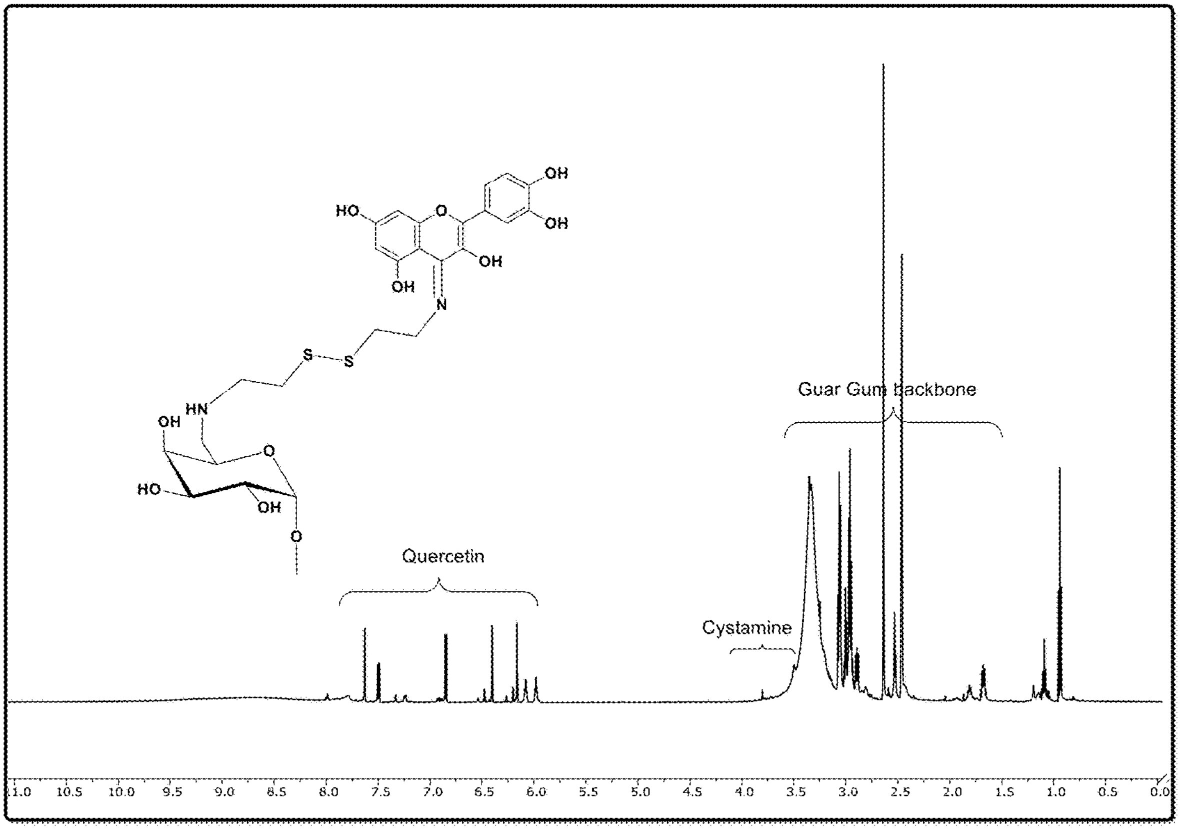
FIG. 5 shows a representative $^1$HNMR spectrum of GG-Cys-Quer Conjugate.
Figure 6:
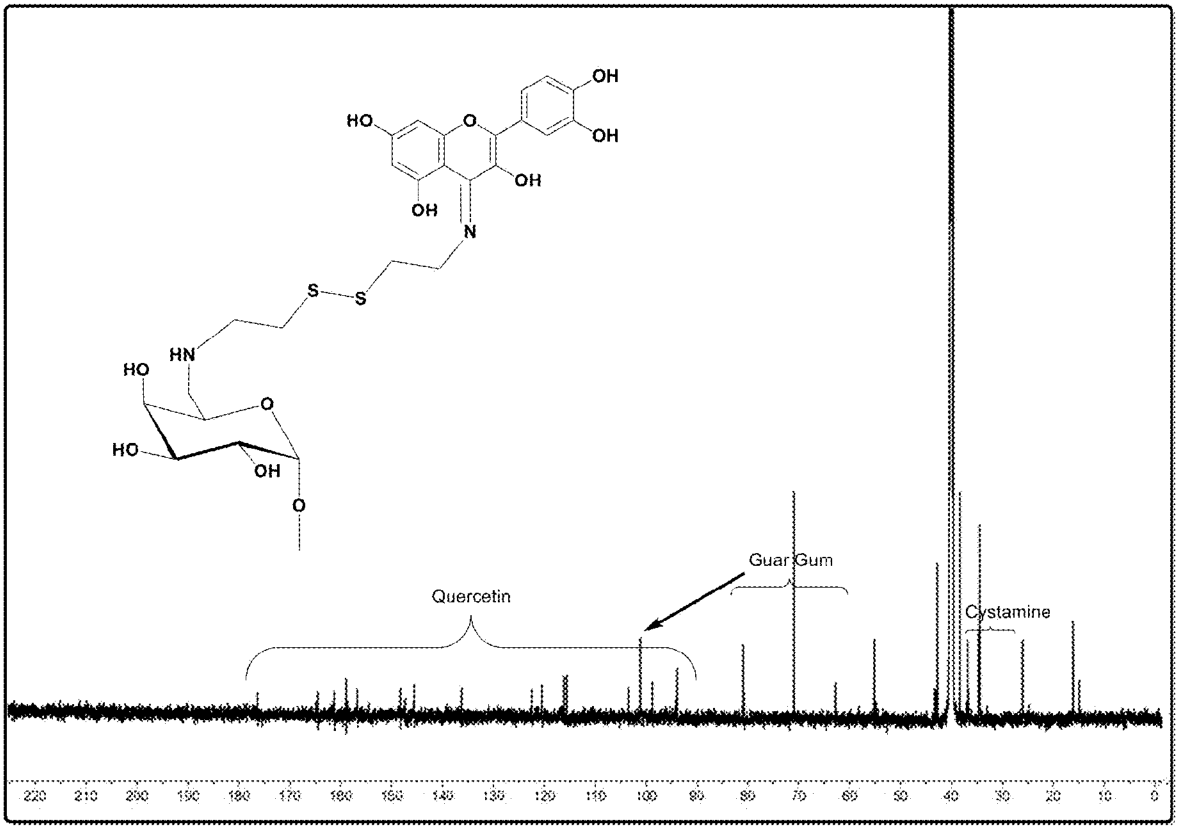
FIG. 6 shows a representative $^{13}$CNMR spectrum of GG-Cys-Quer Conjugate.

The successful incorporation of Cys-Quer intermediate into the guar gum framework was confirmed by the distinct resonances observed in both 1H NMR and $^{13}$C NMR spectrum of the GG-Cys-Quer conjugate. The 1H NMR spectrum (FIG. 5) prominently exhibited broad multiplets in the region of δ 3.3-1.7 ppm, which correspond to the backbone protons of guar gum, particularly those associated with the anomeric and ring protons of the galactomannan matrix, in addition to these characteristic signals. The carbon atoms within the guar gum backbone are responsible for the distinct resonances observed at δ 101.0, 80.5, 70.6, and 63.2 ppm in the $^{13}$C NMR spectrum of GG-Cys-Quer (FIG. 6). These resonances are indicative of the presence of a variety of sugar moieties and their unique structural environments. The anomeric carbon of both mannose and galactose units, which are characteristic of β- and α-glycosidic linkages, is represented by the peak at δ 101 ppm. The signals at δ 80.5 and 70.6 ppm are indicative of ring carbons in the pyranose forms, which are frequently involved in glycosidic bonding or influenced by branching in the galactomannan structure. The C-6 carbon, which may be a component of side chains or involved in functional group modifications in derivative forms, is the typical source of the δ 63.2 ppm peak. The complex chemical environment in the modified guar gum structure is reflected in this spectral overlap, which is induced by branching, hydrogen bonding, and potential conformational constraints. The coexistence of quercetin's aromatic and hydroxyl proton resonances with cystamine's aliphatic peaks, superimposed on guar gum's polysaccharide backbone, offers compelling evidence of effective conjugation and suggests the formation of a structurally integrated GG-Cys-Quer conjugate.

Morphologicial Studies

Figure 7:
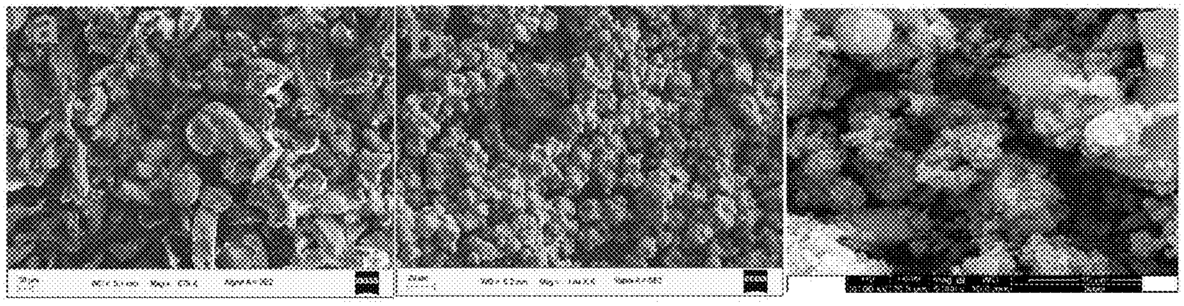
FIG. 7 shows representative SEM images of (a) GG (b) Cys-Quer and (c) GG-Cys-Quer Conjugate

Referring to FIG. 7, GG shows fibrous, folded architecture with irregular topology, typical of unmodified polysaccharides, showcasing natural entanglement and hydrogen-bonded networks (FIG. 7*a*). Cys-Quer shows finely distributed, granular particles with a tendency toward clustering with more ordered and compact, indicating molecular-level interactions between quercetin and cystamine (FIG. 7*b*). GG-Cys-Quer Conjugate shows integrated fibrous-granular matrix, highlighting the successful complexation of GG with Cys-Quer intermediate with dense and uniform with visible particulate domains over polysaccharide folds (FIG. 7*c*).

Thermogravimetry Analysis

Figure 8:
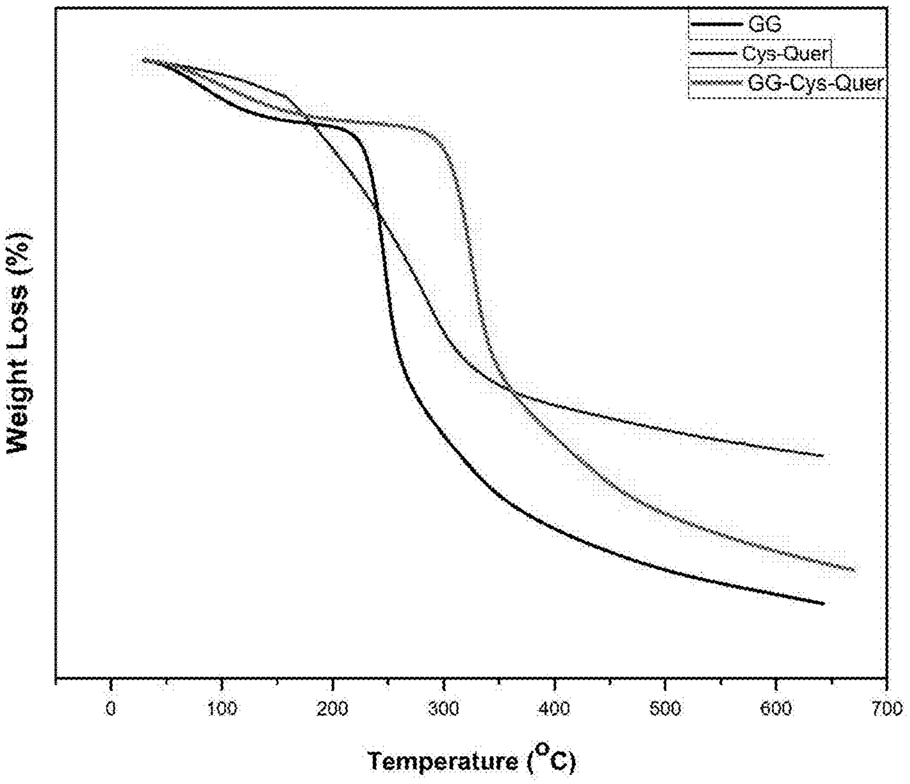
FIG. 8 illustrates TGA of GG, Cys-Quer and GG-Cys-Quer Conjugate.

The thermal degradation investigation of guar gum demonstrated a multi-phase decomposition pattern with the initial degradation phase began at around 70° C., resulting in a weight loss of nearly 9% as shown in FIG. 8. The first mass drop is mainly due to the evaporation of volatile components and the liberation of loosely bound moisture within the polymer matrix. This behavior is characteristic of hydrophilic polysaccharides, which retain water via hydrogen bonding and surface adsorption. The most notable thermal decomposition emerged within the temperature range of 230-380° C., during which a maximum weight loss of around 59% was observed. This significant breakdown indicates the cleavage of the primary polymeric backbone, primarily consisting of galactomannan sugar units. The cleavage of glycosidic bonds under high thermal stress causes the disintegration of the macromolecular structure, culminating in the liberation of low-molecular-weight fragments and volatile degradation products. In Cys-Quer intermediate a preliminary weight loss near 100° C. indicates the evaporation of adsorbed moisture and remaining solvents. The principal decomposition phase, occurring between 150-310° C., entails significant mass loss resulting from the disintegration of the conjugated backbone, including the cleavage of C—C and C—O bonds in the aromatic and aliphatic domains. This phase illustrates the disintegration of quercetin's polyphenolic rings and cystamine's aliphatic chains. GG-Cys-Quer conjugate (GGQC1) showed a synergistic thermal behavior resulting from the combination of a guar gum, a disulfide-containing linker, and a polyphenolic antioxidant quercetin. Initially, a slight weight reduction below 100° C. is noted, ascribed to the evaporation of residual moisture and volatile solvents, characteristic of hydrophilic biopolymers such as guar gum. The principal decomposition transpires between 300-390° C., when substantial weight loss indicates the disintegration of the conjugated structure: the galactomannan backbone of guar gum experiences glycosidic bond cleavage, the aliphatic chains of cystamine deteriorate, and the aromatic rings of quercetin fragment. Above 400° C., residual char may remain, signifying the creation of persistent carbonaceous byproducts. The TGA profile indicates that conjugation improves thermal stability relative to individual components, underscoring its potential for biomedical and industrial applications that necessitate moderate thermal resistance Antifungal Activity of Test Compound Towards *C. auris* Planktonic Cells Table 1 shows the MIC and MFC values for caspofungin and the test compound against five clinical strains of *C. auris*. The data demonstrates that MRL6057 displayed an elevated resistance level against the standard antifungal agent caspofungin, which was 4 μg/mL. The compound showed strong antifungal activity ranging from 0.030 to 0.245 μg/mL against all the tested resistant *C. auris* strain. In addition, the fungicidal activity of the test compound was also evaluated by determining the MFC values of conjugate GGQC1 against the tested strains. The MFC values were one to two-folds higher than the MIC values determining the fungicidal activity of conjugate GGQC1 against all the tested *C. auris* strains.

TABLE 2

MIC and MFC of the conjugate and caspofungin against *C. auris* strains.

| | | Conjugate GGQC1 | |
|---|---|---|---|
| Strains | Caspofungin (MIC; μg/mL) | MIC (μg/mL) | MFC (μg/mL) |
| MRL2921 (CAU1) | 0.125 | 0.061 | 0.245 |
| MRL4000 (CAU2) | 0.125 | 0.030 | 0.123 |
| MRL5762 (CAU3) | 0.125 | 0.061 | 0.123 |
| MRL5765 (CAU4) | 0.25 | 0.061 | 0.245 |
| MRL6057 (CAU5) | 4.0 | 0.245 | 0.488 |

Time-Kill Analysis

Figure 9:
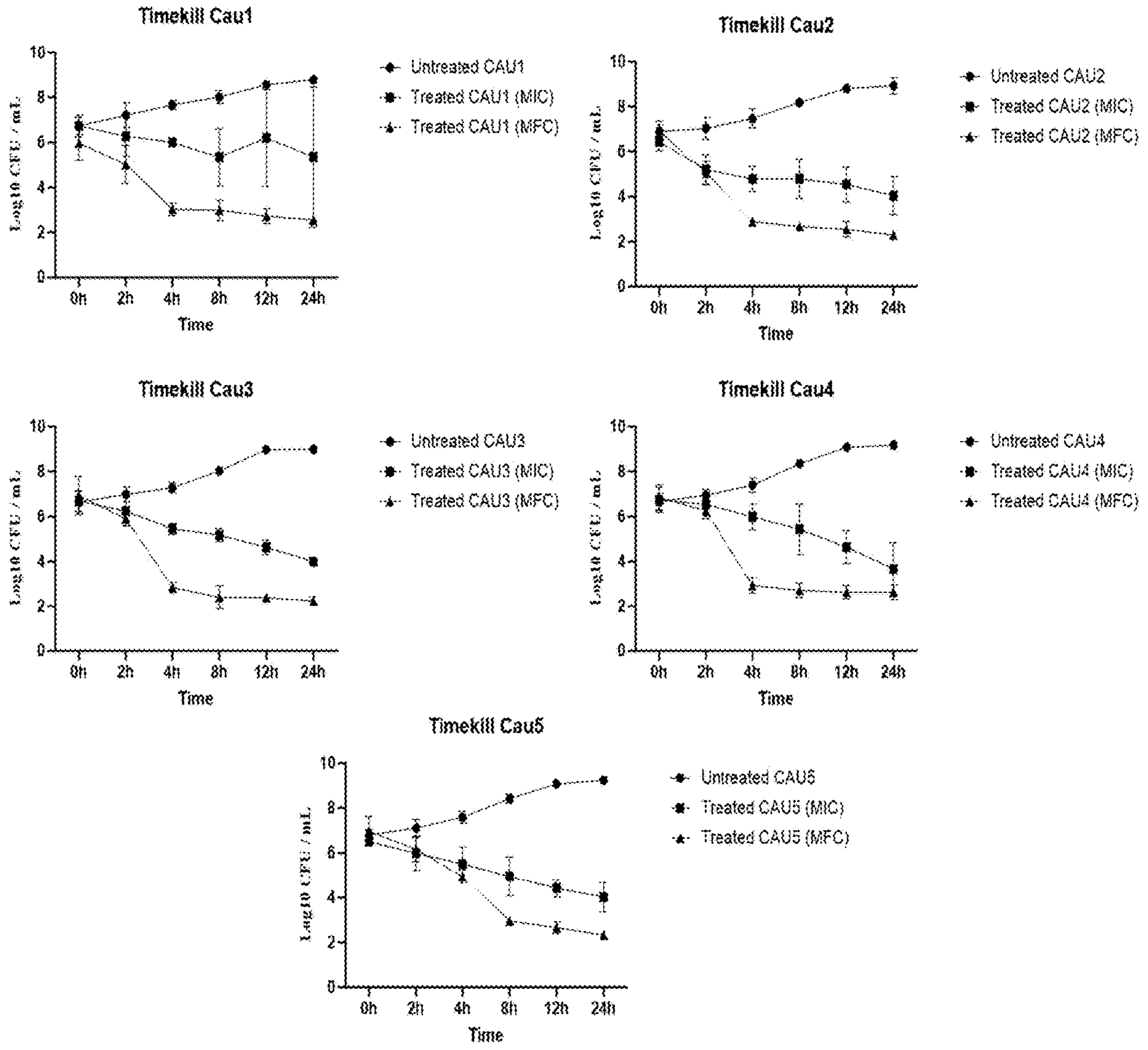
FIG. 9 shows exemplary time-kill curve plots for five *C. auris* strains at various concentrations of test compound (MIC and MFC).

The time-kill curve (FIG. 9) analysis for the test compound against each *C. auris* strain revealed that the compound under investigation exhibited a time and concentration-dependent fungicidal activity (kill of ≥3 log 10 of CFU/mL) against all five strains of *C. auris*. MFC was associated with reaching the ideal endpoint at 24 h across all five strains. Furthermore, for *C. auris* strains CAU1-CAU4 at MFC value, the curve displayed a reduction in yeast growth at 4 h (kill of ≥3 log 10 of CFU/mL), which continued for 24 h., whereas the reduction in the growth of CAU5 was observed after 8 h of incubation. The MIC values also showed a rapid decrease in the growth curve up to 24 h for all the five strains, but the CFU/mL was ≥3 log 10 displaying fungistatic characteristics.

Generally, the time-kill curve is used to understand a drug candidate's -static or -cidal behavior and the association between the dosage and microbial growth over time. Herein, time-kill assays for the test compound against the *C. auris* strains revealed its fungicidal activity at MFC value after 4 h of incubation.

Detection of Total ROS Production

Figure 10A:
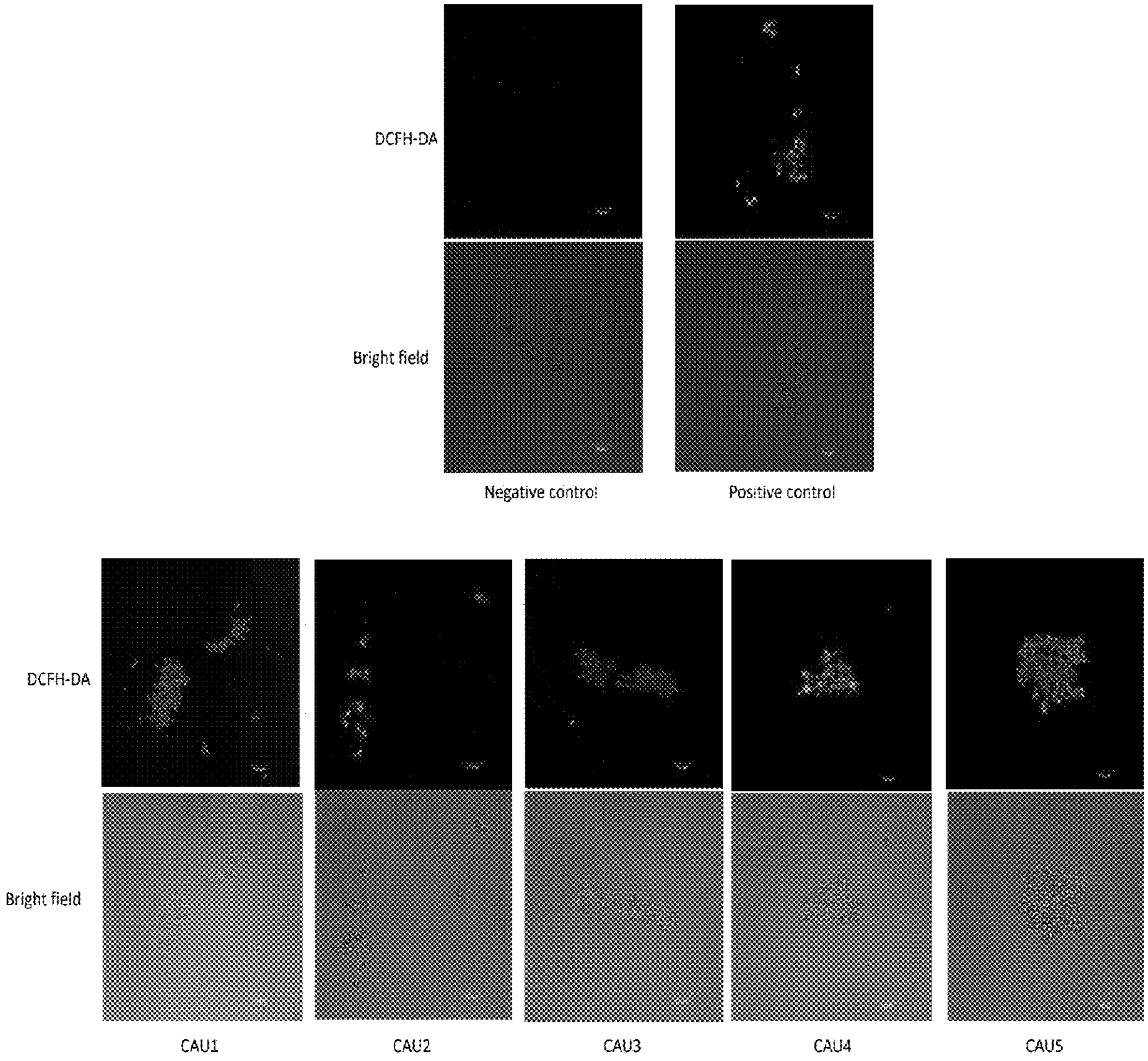
FIGS. 10A and 10B illustrates test compound-mediated ROS generation in *C. auris* strains.
Figure 10B:
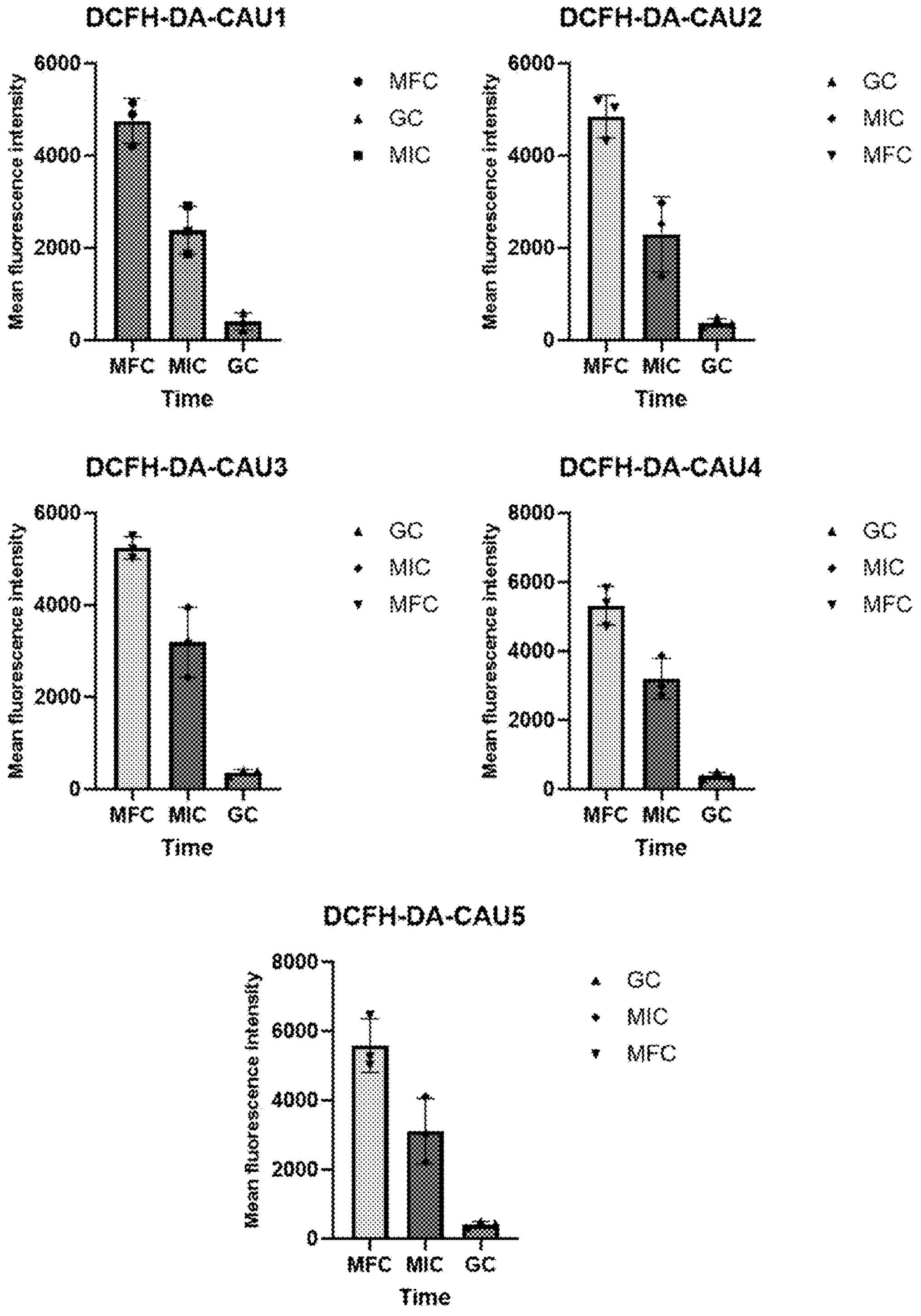

The production of ROS was evaluated to understand the test compound's mode of action in the yeast cells. ROS directly harms yeast cells by inducing and regulating apoptosis. Thus, the capacity to generate extracellular and intracellular ROS directly determines the fungicidal efficacy of the test compound. Herein, DCFH-DA, a fluorescent probe that is a potential indicator of ROS production, was used to spot the generation of intracellular ROS levels with the yeast cells. FIG. 10A demonstrates that after treatment with the test compound, it emitted a strong green fluorescence, while the negative control groups showed no fluorescence. Similarly, FIG. 10B demonstrates that the fluorescence intensity of DCF in the test compound-treated group increased by at least 90% compared with that in the negative control group. This result suggests that the test compound mediated the production and accumulation of ROS in *C. auris* strains.

Gene Expression Studies of Oxidative Stress Enzyme

Figure 11:
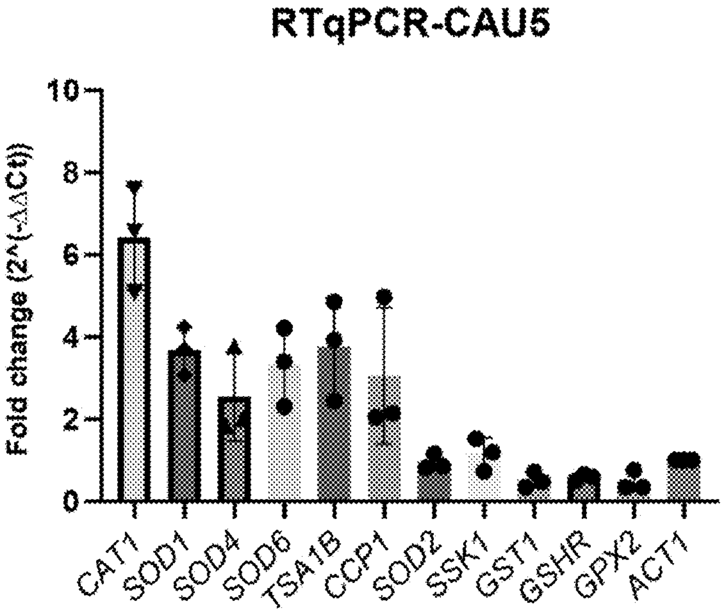
FIG. 11 illustrates expression in oxidative stress-associated enzymes in *C. auris* (CAU5), showing fold change in the expression of antioxidant genes in response to the treatment with the test compound.

The expression of crucial *C. auris* genes (CAT1, SOD1, SOD2, SOD4, SOD6, TSA1B, SSK1, CCP1, GST1, GSHR, and GPX2) associated with the oxidative stress response was studied by RT-qPCR (FIG. 11). After 4 h of exposure to the test compound, six out of the eleven genes studied, CAT1, SOD1, SOD4, SOD6, TSA1B, and CCP1, were overexpressed. The expression of two genes (SOD2 and SSK1) remained unchanged, whereas the remaining three genes (GST1, GSHR, and GPX2) were under-expressed after exposure to the test compound. The modulation in the expression of these genes strongly suggests that the test compound induces oxidative stress in the yeast cell that may trigger cell death by apoptosis.

Mitochondrial Membrane Potential Analysis

Figure 12:
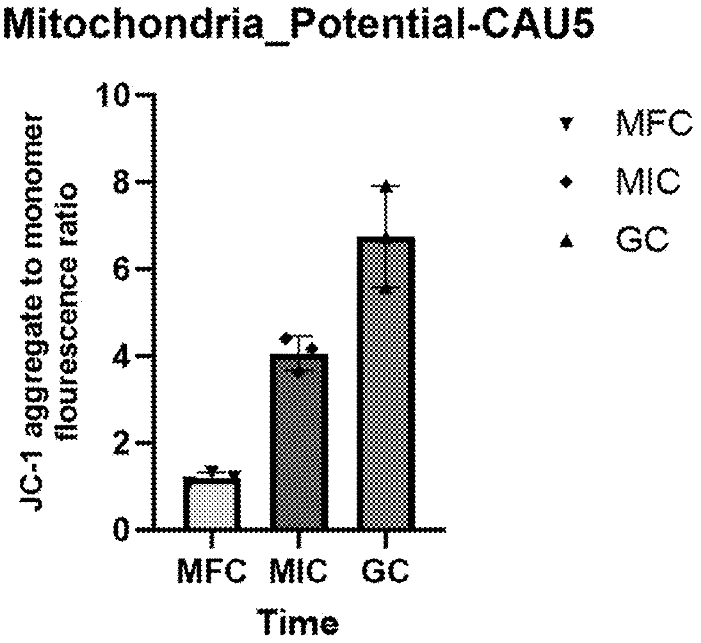
FIG. 12 shows mitochondrial membrane potential, which was evaluated using JC-1 staining.

Mitochondria is a primary target of ROS. Reports suggest that an atypical accumulation of ROS provokes mitochondrial impairment and destabilizes the mitochondrial membrane potential, which eventually leads to cellular apoptosis. High mitochondrial membrane potential results in the accumulation of JC-1 in the mitochondrial matrix, and thus, aggregates of JC-1 dye are formed, releasing a red fluorescence. In contrast, a decrease in mitochondrial membrane potential does not allow the gathering of JC-1. Thus, the JC-1 monomers accumulate in the mitochondrial matrix, generating a green fluorescence. Herein, the data recorded clearly showed that upon treatment of *C. auris* with the test compound, the JC-1 aggregates/monomers ratio decreased compared to the control group (FIG. 12), indicating a loss or destabilization of mitochondrial membrane potential and mitochondrial damage.

Apoptotic Detection

Figure 13:
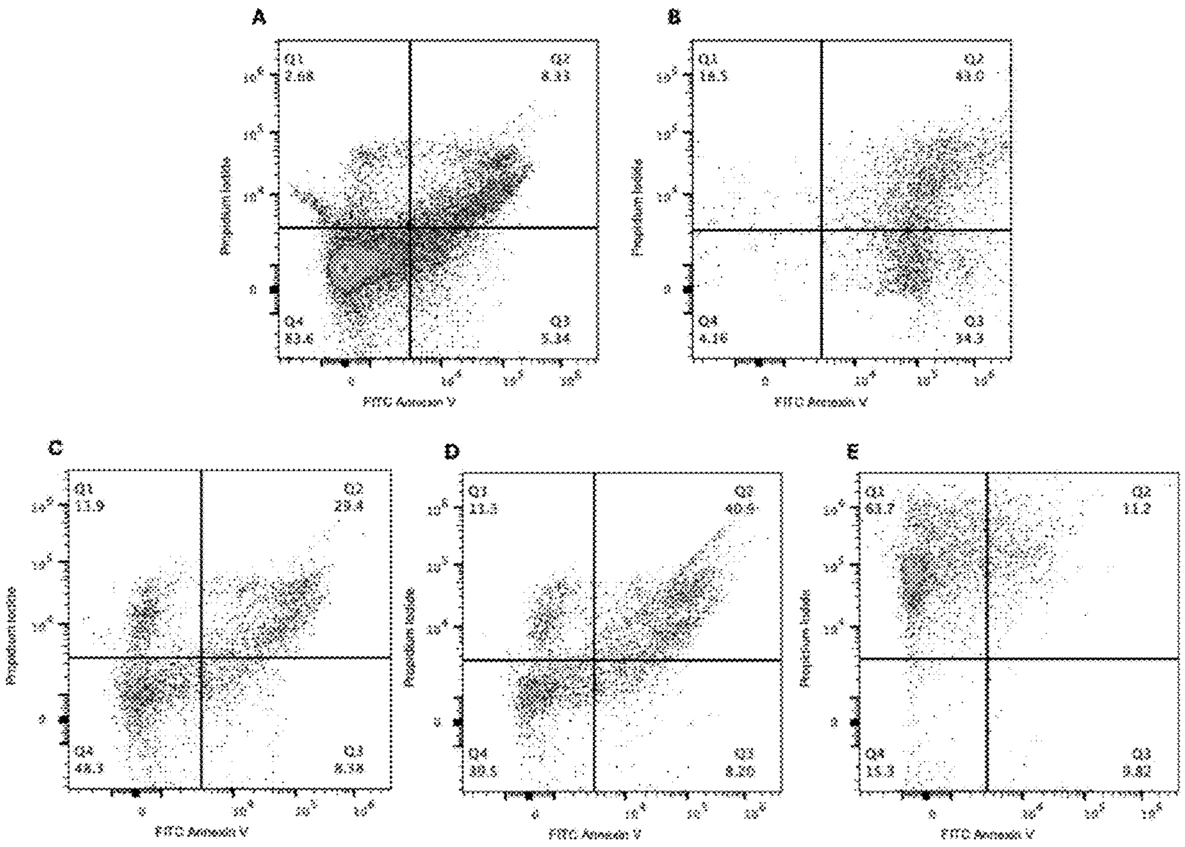
FIG. 13 demonstrates apoptosis of *C. auris* cells by staining with Annexin V-FITC and PI.

In a parallel experiment, annexin V/PI staining was used to validate the route of cellular killing provoked by the test compound. The phosphatidylserine is generally present on the inner side of the plasma membrane, whereas, during apoptosis, the phosphatidylserine is exposed to the outside. This changed behavior is considered an early marker of cellular apoptosis in yeast. The annexin V dye exclusively binds to the externalized phosphatidylserine, and the damaged cells get stained only by PI. FIG. 13 demonstrates that the negative control group has a large viable cell population (83%) with a few staining for apoptotic cells (about 13% apoptotic cells). Whereas the test compound treated *C. auris* cells present a large number of apoptotic cell populations (49% apoptotic cells) at MIC values, revealing that the test compound induced cellular apoptosis in *C. auris*. At higher concentrations, majority of cells showed necrotic cell death with 63% PI positive cells.

Cytotoxicity Assay

Figure 14:
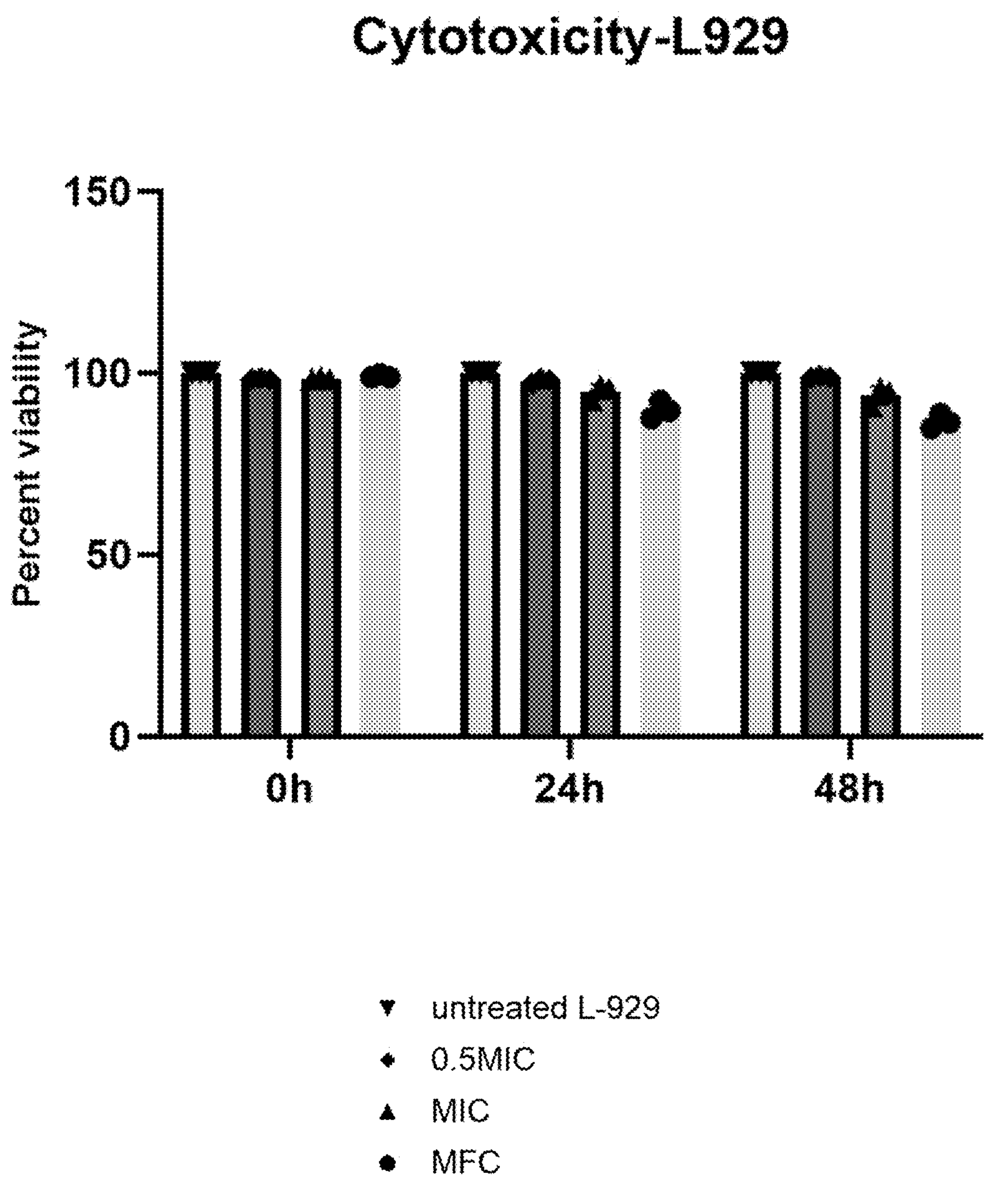
FIG. 14 demonstrates cell toxicity evaluation of an exemplary test compound on mouse fibroblast L929 cells for 0 h, 24 h, and 48 h of incubation.

In vitro cytotoxicity assays are useful for testing candidate drug molecules and predicting human toxicity. Mouse fibroblast L929 cells are considered an excellent model for evaluating in vitro chemical toxicity. Herein, we used L929 cells to inspect the toxicity of the test compound. The data obtained from the CCK-8 assay indicated that the test compound resulted in minor cytotoxicity toward L929 cells after 24 and 48 hours of incubation (FIG. 14). In comparison to the negative control, the average cellular viability of L929 cells in the MFC-treated test compound were 89.93% and 86.71% after 24 and 48 h, respectively, which means that the test compound has a slight cytotoxicity to L929 cells.

Acknowledgement: This work was funded by the University of Jeddah, Jeddah, Saudi Arabia, under grant No.

(UJ-24-SUTU-20551). The authors, therefore, thank the University of Jeddah for its technical and financial support.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

What is claimed is:

1. A quercetin conjugate antifungal entity, comprising:
quercetin;
guar gum; and
a cystamine linker joining the quercetin to the guar gum, wherein the cystamine linker comprise a redox-responsive disulfide bond enabling intracellular cleavage and controlled release of quercetin and wherein the conjugate mediated reactive oxygen species (ROS), induced oxidative stress-associated genes, induced mitochondrial membrane potential, and apoptosis of *Candida auris*.

2. The antifungal entity of claim 1 wherein the quercetin is covalently coupled to the cystamine linker and the cystamine linker is covalently coupled to the guar gum.

3. The antifungal entity of claim 1, wherein the antifungal entity has the general structure

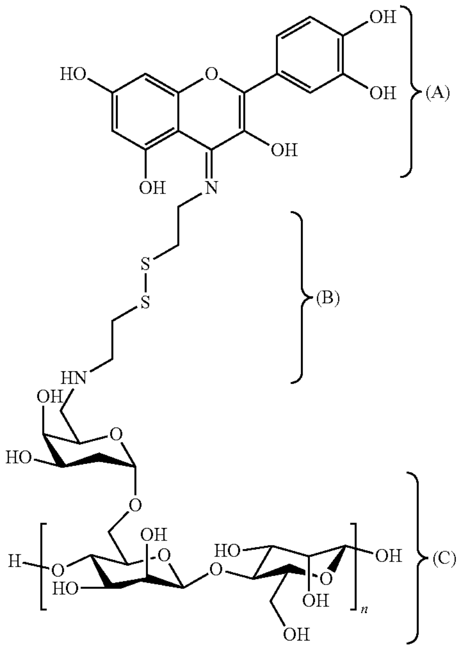

wherein

A is quercetin;

B is a cystamine linker; and

C is guar gum, where n is an integer representing a number of repeating saccharide units of the guar gum.

4. A pharmaceutical composition, comprising:

an antifungal entity of claim 1; and a pharmaceutically acceptable carrier, excipient, or diluent.

5. The pharmaceutical composition of claim 4, wherein the pharmaceutical composition is formulated for administration via a route selected from the group consisting of oral, topical, intravenous, or inhalation.

* * * * *